US011219556B2

(12) United States Patent
Meisner et al.

(10) Patent No.: US 11,219,556 B2
(45) Date of Patent: Jan. 11, 2022

(54) MANUFACTURING PROCESSES FOR ABSORBENT ARTICLES WITH IMPROVED SIDE SEAM BONDING

(71) Applicant: Kimberly-Clark Worldwide, Inc., Neenah, WI (US)

(72) Inventors: Michael D. Meisner, De Pere, WI (US); John W. Hoffman, Appleton, WI (US); John J. Garcia, Neenah, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 0 days.

(21) Appl. No.: 17/047,113

(22) PCT Filed: Apr. 30, 2018

(86) PCT No.: PCT/US2018/030136
§ 371 (c)(1),
(2) Date: Oct. 13, 2020

(87) PCT Pub. No.: WO2019/212469
PCT Pub. Date: Nov. 7, 2019

(65) Prior Publication Data
US 2021/0154051 A1 May 27, 2021

(51) Int. Cl.
*A61F 13/15* (2006.01)
(52) U.S. Cl.
CPC .. *A61F 13/15739* (2013.01); *A61F 13/15585* (2013.01); *A61F 13/15747* (2013.01);
(Continued)

(58) Field of Classification Search
None
See application file for complete search history.

(56) References Cited

U.S. PATENT DOCUMENTS

| 5,733,411 A | 3/1998 | Bett |
| 6,123,792 A | 9/2000 | Samida et al. |

(Continued)

FOREIGN PATENT DOCUMENTS

| CN | 205735997 U | 11/2016 |
| CN | 205853363 U | 1/2017 |

(Continued)

OTHER PUBLICATIONS

Dove, Stacey, "Herrmann Ultraschall cross seal patents", https://www.sustainablenonwovens.net/index.php?option=com_content&view=article&id=13030%3Aherrmann-ultraschall-cross-seal-patents&catid=111%3Amanufacturing-premium&am&Itemid=12.

(Continued)

*Primary Examiner* — Barbara J Musser
(74) *Attorney, Agent, or Firm* — Kimberly-Clark Worldwide, Inc.

(57) ABSTRACT

Methods for forming absorbent articles and side seam bonds of absorbent articles are described. In one embodiment, a method of forming absorbent articles may comprise advancing webs, coupling absorbent cores to the webs intermittently to form open absorbent article chassis, folding the absorbent article chassis, forming a first side seam bond first bond pair between a first region of the webs and a second region of the webs with a first ultrasonic horn, forming a second side seam bond of the bond pair between the first region and the second region with a second ultrasonic horn, the first bond being associated with a first absorbent article chassis and the second side seam bond being associated with a second absorbent article chassis, and cutting the folded absorbent article chassis between the first bond and the second bond to separate the first absorbent article chassis from the second absorbent article chassis.

20 Claims, 5 Drawing Sheets

(52) U.S. Cl.
CPC .............. *A61F 13/15804* (2013.01); *A61F 2013/15869* (2013.01)

(56) References Cited

U.S. PATENT DOCUMENTS

| | | |
|---|---|---|
| 6,454,890 B1 | 9/2002 | Couillard et al. |
| 6,667,085 B1 | 12/2003 | McNichols |
| 6,976,521 B2 | 12/2005 | Mlinar et al. |
| 7,179,343 B2 | 2/2007 | VanEperen et al. |
| 7,452,320 B2 | 11/2008 | Csida et al. |
| 7,887,656 B2 * | 2/2011 | Yamamoto ........ B29C 66/81467 156/73.1 |
| 8,206,365 B2 | 6/2012 | Norrby |
| 8,323,167 B2 | 12/2012 | Berggren et al. |
| 8,669,412 B2 | 3/2014 | Fernkvist et al. |
| 8,853,487 B2 | 10/2014 | Takeuchi et al. |
| 8,925,607 B2 | 1/2015 | Yamamoto |
| 9,138,937 B2 | 9/2015 | Frank et al. |
| 9,248,056 B2 | 2/2016 | Sablone et al. |
| 2002/0074079 A1 | 6/2002 | Reynolds et al. |
| 2003/0188819 A1 | 10/2003 | Campbell et al. |
| 2004/0102757 A1 | 5/2004 | Olson |
| 2005/0145317 A1 | 7/2005 | Yamamoto |
| 2016/0107377 A1 * | 4/2016 | Fujita ............... A61F 13/15804 156/73.1 |
| 2017/0027763 A1 | 2/2017 | Fujita et al. |
| 2018/0071152 A1 * | 3/2018 | Schuette ............. B29C 66/8412 |

FOREIGN PATENT DOCUMENTS

| | | |
|---|---|---|
| CN | 106999309 A | 8/2017 |
| EP | 2886089 A1 | 6/2015 |
| JP | H10290818 A | 11/1998 |
| JP | 2002219145 A | 8/2002 |
| JP | 2012120775 A | 6/2012 |
| JP | 2015062634 A | 4/2015 |
| JP | 2015116250 A | 6/2015 |
| JP | 2016215281 A | 12/2016 |
| WO | 05105410 A1 | 11/2005 |
| WO | 14200102 A1 | 12/2014 |

OTHER PUBLICATIONS

Altrasonic "Ultrasonic Bonding of Nonwovens, Films and Textiles", http://www.altrasonic.com/Ultrasonic-Bonding-Of-Nonwovens-Films-And-Textiles_n28.

* cited by examiner

MANUFACTURING PROCESSES FOR ABSORBENT ARTICLES WITH IMPROVED SIDE SEAM BONDING

TECHNICAL FIELD

The present disclosure relates to absorbent articles and methods of manufacturing absorbent articles. More specifically, the present disclosure is directed toward absorbent articles with improved side seam bonds and methods for manufacturing such absorbent articles.

BACKGROUND OF THE DISCLOSURE

People rely on disposable absorbent products in their everyday lives, including such articles as adult incontinence products, enuresis pants, training pants, and diapers. Many manufacturers seek to better meet the needs of users of such products and improve manufacturing process for forming such absorbent articles.

One method of manufacturing such absorbent articles is term a cross-direction (CD) method of manufacturing. An example prior art CD manufacturing method 100 is shown with respect to FIG. 1. As shown in FIG. 1, the method 100 may generally comprise extending one or more continuous webs 102 in the manufacturing direction (MD). The one or more webs 102 may comprise the front waist panel 103 and the rear waist panel 105 of finished absorbent articles 10 formed by the manufacturing process 100. A continuously extending length of absorbent cores 104 may be brought to core placement module 110, which may be configured to place individual absorbent cores 104 onto the one or more webs 102. In some embodiments, the core placement module 110 may be configured to form individual absorbent cores 106 by cutting the continuously extending length of absorbent cores 104 into individual absorbent cores 106, rotating the cores 106, and placing the cores 106 intermittently onto the one or more webs 102.

The cores 106 may be positioned onto the one or more webs 102 so as to span a crotch region of the finished absorbent articles 10. As can be seen, the absorbent cores 106 have a generally rectangular shape where a first dimension of the cores is generally greater than a second dimension of the cores. The absorbent cores 106 are placed onto the one or more webs 102 such that the longer dimension of the cores 106 is extending in the direction CD.

Before or after placement of the absorbent cores 106, one or more additional processing steps may be performed and these additional steps may vary according to the specifics of each manufacturing process. Some example additional steps may include, as in the method 100, cutting portions of the one or more continuously extending webs to form leg holes. For example, before placement of the cores 106 onto the one or more webs 102, the one or more webs 102 may be advanced to cutting module 120. The cutting module 120 may comprise a knife roll and an anvil roll, with the knife roll comprising a knife configured in the pattern of the leg cut-out. As the web advances through the module 120, the knife cuts the web in the shape of the leg cut-out and the cut web portion is removed from the one or more webs 102. Additionally, although shown as a step prior to the placement of the absorbent cores 106, forming the leg holes may occur after the cores 106 are placed onto the one or more continuous webs 102. Other steps may include placing a covering layer over the absorbent core and the one or more continuously extending webs to form a liner layer.

These described processing steps generally result in a continuously extending series of absorbent article chassis 112 which are in an open configuration. The chassis 112 may then be advanced to a folding module 130. The folding module 130 may be configured to fold the absorbent article chassis in half such that the one or more webs 102 forming the front and rear waist panels 103, 105 are brought into close proximity.

Next, these folded absorbent article chassis 112 are advanced through a bonding unit 140 which forms bonds 115 between the one or more webs 102 forming the front and rear waist panels 103, 105 of finished absorbent articles 10. Such bonds 115 are termed side seam bonds in the art. Finally, the chassis 112 are advanced through cutting module 150, which cuts the chassis 112 between the side seam bonds 115 to form individual finished absorbent articles 10.

FIG. 2 is a perspective view of one exemplary prior art bonding unit 140 which may be used to form the side seam bonds 115. As can be seen, the bonding unit 140 comprises a rotating anvil unit 146, an ultrasonic horn unit 142, and web guiding rolls 144. The ultrasonic horn unit 142 is connected to an energy source (not shown) through coupling 143 by which the ultrasonic horn unit 142 may be energized to form the side seam bonds 115. The rotating anvil 146 further comprises pairs of extending protrusions 151, 152 which are configured to engage with the ultrasonic horn unit 142 to form the side seam bonds 115.

As can be seen, the bonding unit 140 is configured to form a pair of bonds 115 in quick succession, each of the individual bonds 115A, 115B associated with separate absorbent article chassis 112. For instance, the first bond of the bond pair 115, e.g. bond 115A, which is the leading bond in the machine direction MD, forms a side seam bond of a first absorbent article chassis 112, and the second bond of the bond pair 115, e.g. bond 115B, which is the trailing bond in the machine direction MD, forms a side seam bond of a second absorbent article chassis 112. The second absorbent article chassis 112 is connected to and immediately trails the first absorbent article chassis 112 in the machine direction MD.

The present disclosure relates to absorbent articles and methods of manufacturing absorbent articles. More specifically, the present disclosure is directed toward absorbent articles with improved side seam bonds and methods for manufacturing such absorbent articles.

SUMMARY OF THE DISCLOSURE

The present disclosure relates to absorbent articles, and more specifically absorbent articles with improved side seam bonds.

In a first embodiment, a method of forming absorbent articles may comprise advancing one or more continuous webs in a machine direction, a first region of the one or more continuous webs comprising a front waist panel material and a second region of the one or more continuous webs comprising a rear waist panel material, coupling absorbent cores to the one or more continuous webs intermittently to form an interconnected series of open absorbent article chassis, each absorbent article chassis comprising a front waist panel, a rear waist panel, and an absorbent core extending between the front waist panel and the rear waist panel, folding the interconnected series of open absorbent article chassis to form an interconnected series of closed absorbent article chassis, forming a first side seam bond of a first side seam bond pair between the first region of the one or more continuous webs and the second region of the one or more continuous webs with a first ultrasonic horn, forming a second side seam bond of the first side seam bond pair between the first region of the one or more continuous webs and the second region of the one or more continuous webs with a second ultrasonic horn, wherein the first side seam bond of the first side seam bond pair is associated with a first absorbent article chassis and wherein the second side seam bond of the first side seam bond pair is associated with a second absorbent article chassis, and cutting the interconnected series of folded absorbent article chassis between the first side seam bond and the second side seam bond of the first side seam bond pair to separate the first absorbent article chassis from the second absorbent article chassis.

In a second embodiment, the method of the first embodiment may further comprise forming a first side seam bond of a second side seam bond pair between the first region of the one or more continuous webs and the second region of the one or more continuous webs with the first ultrasonic horn, forming a second side seam bond of the second side seam bond pair between the first region of the one or more continuous webs and the second region of the one or more continuous webs with a second ultrasonic horn, wherein the first side seam bond of the second side seam bond pair is associated with the second absorbent article chassis and wherein the second side seam bond of the second side seam bond pair is associated with a third absorbent article chassis, and cutting the interconnected series of folded absorbent article chassis between the first side seam bond of the second side seam bond pair and the second side seam bond of the second side seam bond pair to separate the second absorbent article chassis from the third absorbent article chassis.

In a third embodiment, the method of any of the first or second embodiments may further comprise forming a first side seam bond of a second side seam bond pair between the first region of the one or more continuous webs and the second region of the one or more continuous webs with the first ultrasonic horn, forming a second side seam bond of the second side seam bond pair between the first region of the one or more continuous webs and the second region of the one or more continuous webs with a second ultrasonic horn, wherein the first side seam bond of the second side seam bond pair is associated with a third absorbent article chassis and wherein the second side seam bond of the second side seam bond pair is associated with the second absorbent article chassis, and cutting the interconnected series of folded absorbent article chassis between the first side seam bond of the second side seam bond pair and the second side seam bond of the second side seam bond pair to separate the second absorbent article chassis from the third absorbent article chassis.

In a fourth embodiment, the method of the third embodiment may further comprise forming a first side seam bond of a third side seam bond pair between the first region of the one or more continuous webs and the second region of the one or more continuous webs with the first ultrasonic horn, forming a second side seam bond of the third side seam bond pair between the first region of the one or more continuous webs and the second region of the one or more continuous webs with a second ultrasonic horn, wherein the first side seam bond of the third side seam bond pair is associated with the third absorbent article chassis and wherein the second side seam bond of the third side seam bond pair is associated with a fourth absorbent article chassis, forming a first side seam bond of a fourth side seam bond pair between the first region of the one or more continuous webs and the second region of the one or more continuous webs with the first ultrasonic horn, forming a second side seam bond of the fourth side seam bond pair between the first region of the one or more continuous webs and the second region of the one or more continuous webs with a second ultrasonic horn, wherein the first side seam bond of the fourth side seam bond pair is associated with a fifth absorbent article chassis and wherein the second side seam bond of the fourth side seam bond pair is associated with the fourth absorbent article chassis, and cutting the interconnected series of folded absorbent article chassis between the first side seam bond of the third side seam bond pair and the second side seam bond of the third side seam bond pair and between the first side seam bond of the fourth side seam bond pair and the second side seam bond of the fourth side seam bond pair to separate the third absorbent article chassis from the fourth absorbent article chassis and the fourth absorbent article chassis from the fifth absorbent article chassis.

In a fifth embodiment, the third embodiment may further comprise forming a first side seam bond of a third side seam bond pair between the first region of the one or more continuous webs and the second region of the one or more continuous webs with the first ultrasonic horn, forming a second side seam bond of the third side seam bond pair between the first region of the one or more continuous webs and the second region of the one or more continuous webs with a second ultrasonic horn, wherein the first side seam bond of the third side seam bond pair is associated with a fourth absorbent article chassis and wherein the second side seam bond of the third side seam bond pair is associated with the third absorbent article chassis, forming a first side seam bond of a fourth side seam bond pair between the first region of the one or more continuous webs and the second region of the one or more continuous webs with the first ultrasonic horn, forming a second side seam bond of the fourth side seam bond pair between the first region of the one or more continuous webs and the second region of the one or more continuous webs with a second ultrasonic horn, wherein the first side seam bond of the fourth side seam bond pair is associated with the fourth absorbent article chassis and wherein the second side seam bond of the fourth side seam bond pair is associated with a fifth absorbent article chassis, and cutting the interconnected series of folded absorbent article chassis between the first side seam bond of the third side seam bond pair and the second side seam bond of the third side seam bond pair and between the first side seam bond of the fourth side seam bond pair and the second side seam bond of the fourth side seam bond pair to separate the third absorbent article chassis from the fourth absorbent article chassis and the fourth absorbent article chassis from the fifth absorbent article chassis.

In a sixth embodiment, first side seam bond of the first side seam bond pair of any of the first through fifth embodiments may be formed by the first ultrasonic horn engaging a first anvil, and the second side seam bond of the first side seam bond pair of any of the first through fifth embodiments may be formed by the second ultrasonic horn engaging with a second anvil.

In a seventh embodiment, the second ultrasonic horn of the sixth embodiment is spaced from the first ultrasonic horn a distance of at least 1.0 m in the manufacturing direction.

In an eighth embodiment, the first side seam bond of the first side seam bond pair of any of the first through seventh embodiments may be formed by the first ultrasonic horn engaging a first anvil, and the second side seam bond of the first side seam bond pair of any of the first through seventh embodiments may be formed by the second ultrasonic horn engaging with the first anvil.

In a ninth embodiment, the first ultrasonic horn of any of the first through eighth embodiments may be spaced away from the second ultrasonic horn on the first anvil a circumferential distance greater than or equal to twenty-percent of the circumference of the first anvil.

In a tenth embodiment, a method of forming absorbent articles may comprise advancing one or more continuous webs in a machine direction at a web speed, a first region of the one or more continuous webs comprising a front waist panel material and a second region of the one or more continuous webs comprising a rear waist panel material, wherein the web speed is greater than or equal to 250 m/min, coupling absorbent cores to the one or more continuous webs intermittently to form an interconnected series of open absorbent article chassis, each absorbent article chassis comprising a front waist panel, a rear waist panel, and an absorbent core extending between the front waist panel and the rear waist panel, folding the interconnected series of open absorbent article chassis to form an interconnected series of closed absorbent article chassis, forming a first side seam bond of a first side seam bond pair between the first region of the one or more continuous webs and the second region of the one or more continuous webs with a first ultrasonic horn, forming a second side seam bond of the first side seam bond pair between the first region of the one or more continuous webs and the second region of the one or more continuous webs with a second ultrasonic horn, wherein the first side seam bond of the first side seam bond pair is associated with a first absorbent article chassis and wherein the second side seam bond of the first side seam bond pair is associated with a second absorbent article chassis, and cutting the interconnected series of folded absorbent article chassis between the first side seam bond and the second side seam bond of the first side seam bond pair to separate the first absorbent article chassis from the second absorbent article chassis, wherein the first side seam bond of the first side seam bond pair has a bond strength of greater than or equal to 17 N, according to the Bond Peel Strength Test Method, and wherein the second side seam bond of the first side seam bond pair has a bond strength of greater than or equal to 17 N, according to the Bond Peel Strength Test Method.

In an eleventh embodiment, the first side seam bond of the first side seam bond pair of the tenth embodiment may have a bond strength of greater than or equal to 29 N, according to the Bond Peel Strength Test Method, the second side seam bond of the first side seam bond pair may have a bond strength of greater than or equal to 29 N, according to the Bond Peel Strength Test Method.

In a twelfth embodiment, the web speed of any of the eleventh or twelfth embodiments may be greater than or equal to 300 m/min.

In a thirteenth embodiment, the first side seam bond of the first side seam bond pair of any of the tenth through twelfth embodiments may be formed by the first ultrasonic horn engaging with a first anvil roll, and the second side seam bond of the first side seam bond pair may be formed by the second ultrasonic horn engaging with a second anvil roll.

In a fourteenth embodiment, the second ultrasonic horn of the thirteenth embodiment may be spaced from the first ultrasonic horn a distance of at least 1.0 m in the manufacturing direction.

In a fifteenth embodiment, a difference between the bond strength of the first side seam bond of the first side seam bond pair of any of the tenth through fourteenth embodiments and the second side seam bond of the first side seam bond pair may be less than about 15% of the value of the greater of the bond strength of the first side seam bond of the first side seam bond pair and the second side seam bond of the first side seam bond pair.

In a sixteenth embodiment, a difference between the bond strength of the first side seam bond of the first side seam bond pair of any of the tenth through fourteenth embodiments and the second side seam bond of the first side seam bond pair may be less than about 10% of the value of the greater of the bond strength of the first side seam bond of the first side seam bond pair and the second side seam bond of the first side seam bond pair.

Figure 1:
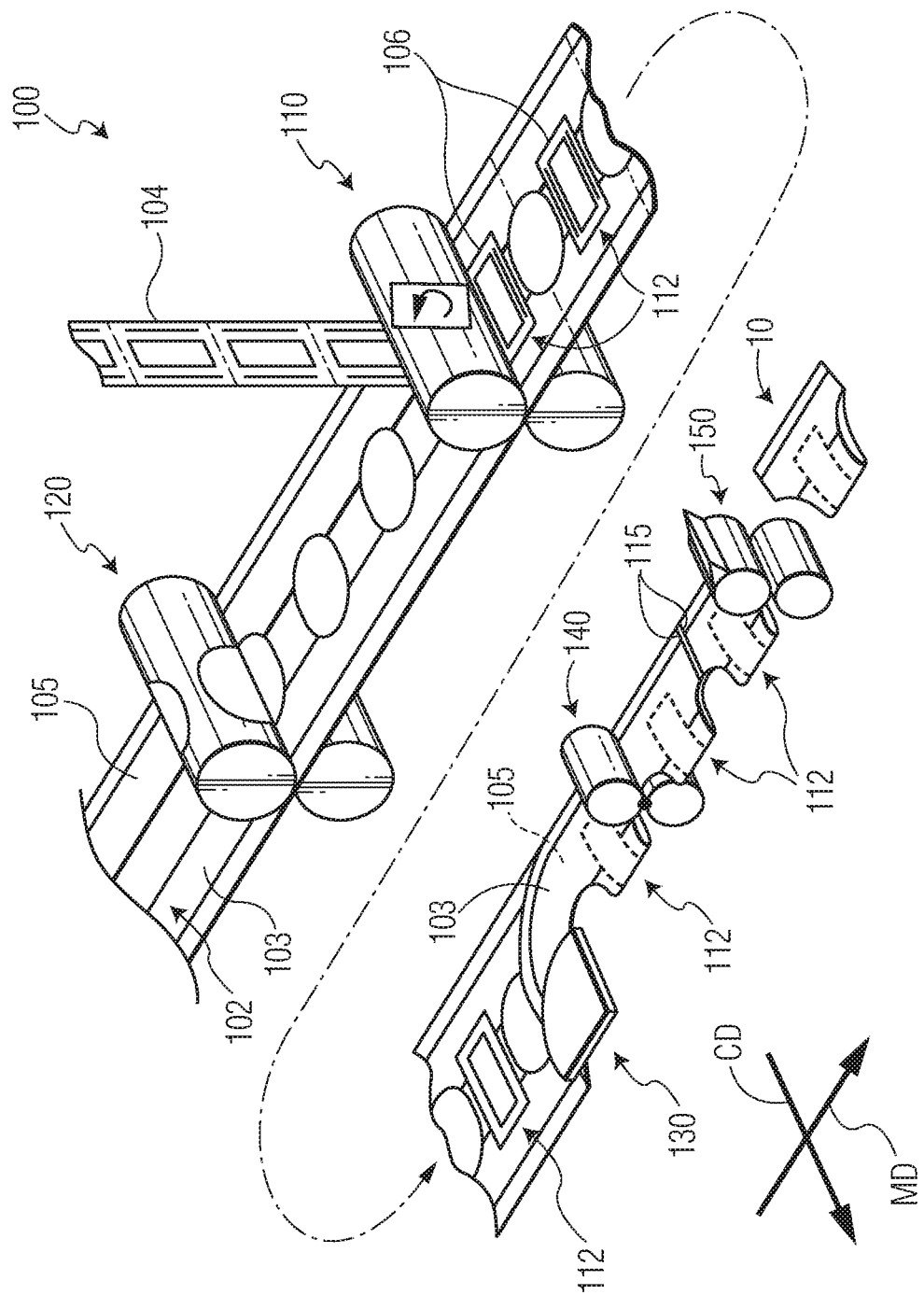
FIG. 1 is a perspective view of a prior art process for forming absorbent articles including side seam bonds.
Figure 2:
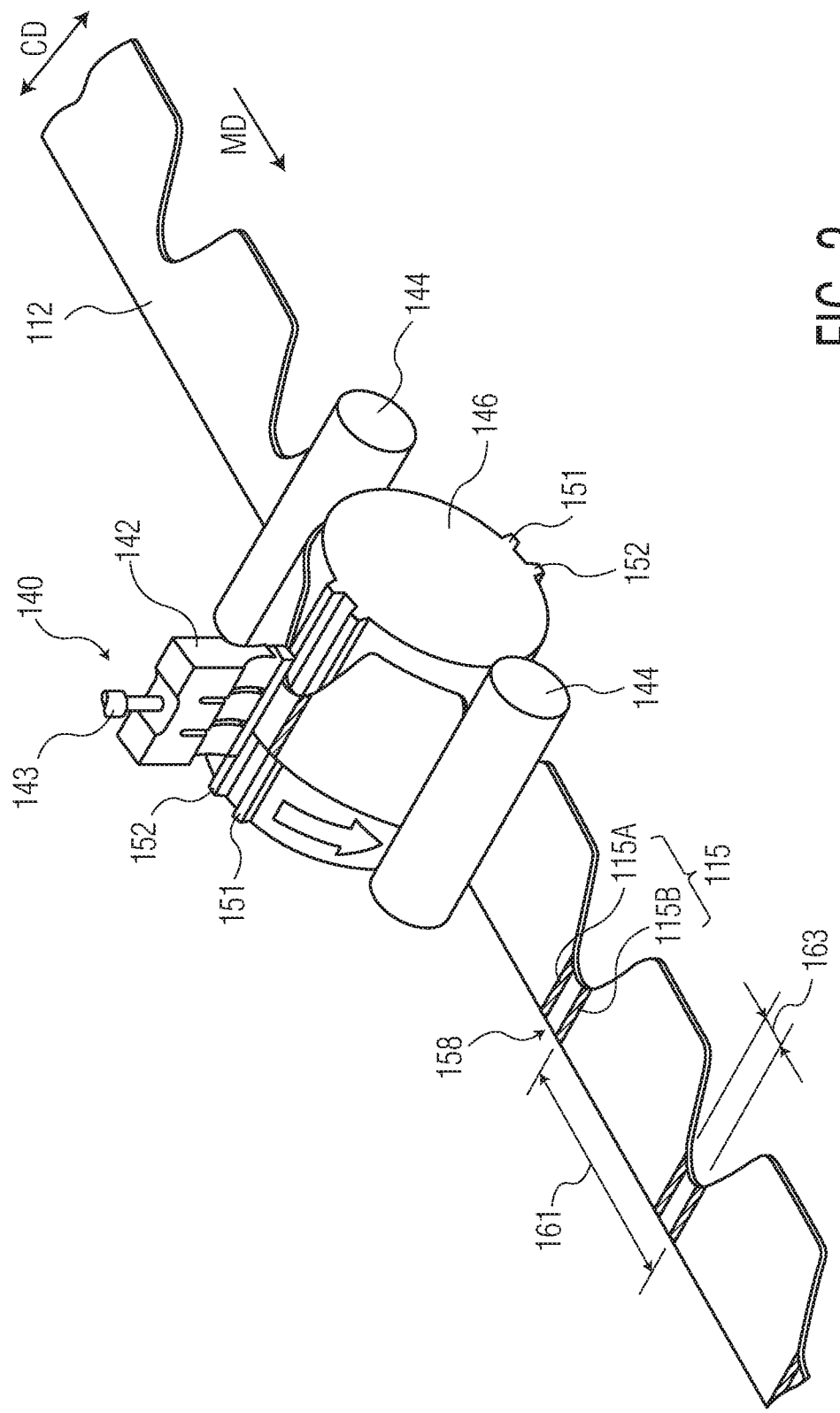
FIG. 2 is a perspective view of a bonding unit for forming side seam bonds in absorbent articles.

While the disclosure is amenable to various modifications and alternative forms, specifics thereof have been shown by way of example in the drawings and will be described in detail. It should be understood, however, that the intention is not to limit aspects of the disclosure to the particular illustrative embodiments described. On the contrary, the intention is to cover all modifications, equivalents, and alternatives falling within the spirit and scope of the disclosure.

DETAILED DESCRIPTION OF THE DISCLOSURE

The present disclosure relates to absorbent articles and methods of manufacturing absorbent articles. More specifically, the present disclosure is directed toward absorbent articles with improved side seam bonds and methods for manufacturing such absorbent articles.

The following description should be read with reference to the drawings in which similar elements in different drawings are numbered the same. The description and the drawings, which are not necessarily to scale, depict illustrative embodiments and are not intended to limit the scope of the disclosure.

Within the context of this specification, each term or phrase below will include the following meaning or meanings. Additional terms are defined elsewhere in the specification.

"Absorbent article" refers herein to an article which may be placed against or in proximity to the body (i.e., contiguous with the body) of the wearer to absorb and contain various liquid, solid, and semi-solid exudates discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, diapers, training pants, youth pants, swim pants, and incontinence products, and the like without departing from the scope of the present disclosure.

"Bonded" refers to the joining, adhering, connecting, attaching, or the like, of two elements. Two elements will be considered bonded together when they are joined, adhered, connected, attached, or the like, directly to one another or indirectly to one another, such as when bonded to an intermediate element. The bonding can occur via, for example, adhesive, pressure bonding, thermal bonding, ultrasonic bonding, stitching, suturing, and/or welding.

"Connected" refers to the joining, adhering, bonding, attaching, or the like, of two elements. Two elements will be considered to be connected together when they are connected directly to one another or indirectly to one another, such as when each is directly connected to intermediate elements.

"Disposable" refers to articles which are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element.

"Machine direction" (MD) refers to the length of a fabric in the direction in which it is produced, as opposed to a "cross-machine direction" (CD) which refers to the width of a fabric in a direction generally perpendicular to the machine direction.

"Nonwoven fabric" or "nonwoven web", or simply "web" refers herein to a web having a structure of individual fibers or threads which are interlaid, but not in an identifiable manner as in a knitted fabric. Nonwoven fabrics or webs have been formed from many processes such as, for example, meltblowing processes, spunbonding processes, through-air bonded carded web (also known as BCW and TABCW) processes, etc.

These terms may be defined with additional language in the remaining portions of the specification.

Figure 3:
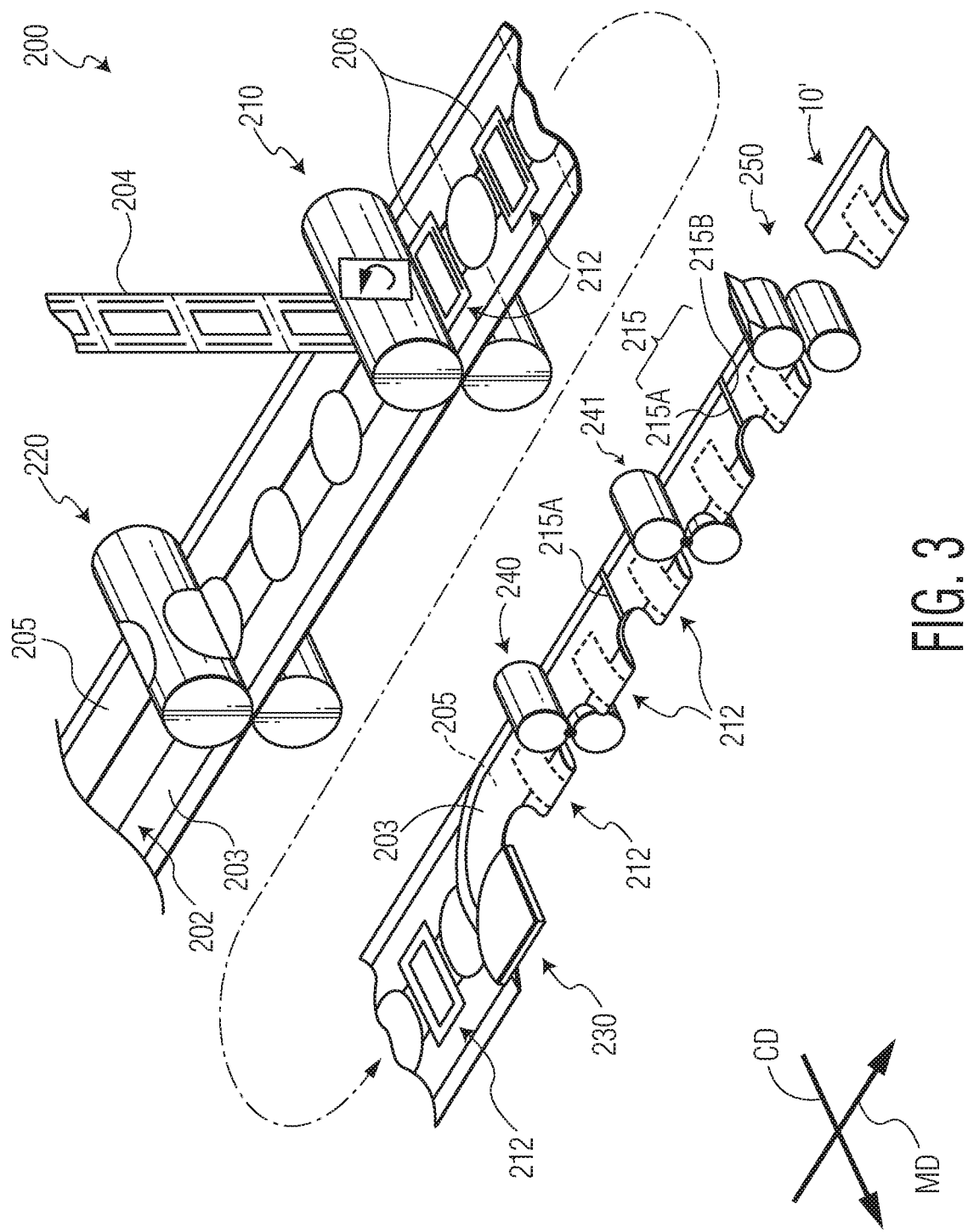
FIG. 3 is a perspective view of a process for forming absorbent articles including side seam bonds, according to aspects of the present disclosure.

FIG. 3 depicts a perspective view of manufacturing method 200, which is an alternative method for manufacturing finished absorbent articles, such as absorbent articles 10', to prior art method 100. The method 200 may include some similarities to method 100. For example, the method 200 may generally comprise extending one or more continuous webs 202 in the manufacturing direction (MD). The one or more webs 202 may comprise the front waist panel 203 and the rear waist panel 205 of finished absorbent articles 10 formed by the manufacturing process 200. A continuously extending length of absorbent cores 204 may be brought to core placement module 210, which may be configured to place individual absorbent cores 204 onto the one or more webs 202. In some embodiments, the core placement module 210 may be configured to form individual absorbent cores 206 by cutting the continuously extending length of absorbent cores 204 into individual absorbent cores 206, rotating the cores 206, and placing the cores 206 intermittently onto the one or more webs 202.

The cores 206 may be positioned onto the one or more webs 202 so as to span a crotch region of the finished absorbent articles 10'. As can be seen, the absorbent cores 206 have a generally rectangular shape where a first dimension of the cores is generally greater than a second dimension of the cores. The absorbent cores 206 are placed onto the one or more webs 202 such that the longer dimension of the cores 206 is extending in the direction CD.

Before or after placement of the absorbent cores 206, one or more additional processing steps may be performed and these additional steps may vary according to the specifics of each manufacturing process. Some example additional steps may include, as in the method 200, cutting portions of the one or more continuously extending webs to form leg holes. For example, after placement of the cores 206 onto the one or more webs 202, the one or more webs 202 including the cores 206 may be advanced to cutting module 220. The cutting module 220 may comprise a knife roll and an anvil roll, with the knife roll comprising a knife configured in the pattern of the leg cut-out. As the web advances through the module 220, the knife cuts the web in the shape of the leg cut-out and the cut web portion is removed from the one or more webs 202. Other steps may include placing a covering layer over the absorbent core and the one or more continuously extending webs to form a liner layer.

These described processing steps generally result in a continuously extending series of absorbent article chassis 212 which are in an open configuration. The chassis 212 may then be advanced to a folding module 230. The folding module 230 may be configured to fold the absorbent article chassis in half such that the one or more webs 202 forming the front and rear waist panels 203, 205 are brought into close proximity.

Next, these folded absorbent article chassis 212 are advanced through a first bonding unit 240 which forms a first bond, bond 215A, of a bond pair 215 between the one or more webs 202 forming the front and rear waist panels 203, 205 of finished absorbent articles 10'. The chassis 112 are then advanced to a second bonding unit 241 which forms a second bond, bond 215B, of a bond pair 215 between the one or more webs 202 of the finished absorbent articles 10. Finally, the chassis 112 are advanced through cutting module 250, which cuts the chassis 212 between the side seam bonds 215A, 215B to form individual finished absorbent articles 10'.

As will be described in further detail below, forming the two bonds 215A, 215B of each bond pair 215 in the above described manner allows for the formation of higher quality bonds than forming such bond pairs 215 according to the prior art method 100. One measure of bond quality may be the strength of a bond. In particular, the method 200 may allow for formation of bonds 215A, 215B which have higher bond strengths than the bonds 215A, 215B formed by the method 100. Further, the strength of each of the bonds 215A, 215B formed according to the method 200 may be more similar to the strengths of the bonds 215A, 215B formed according to the method 100.

Figure 4:
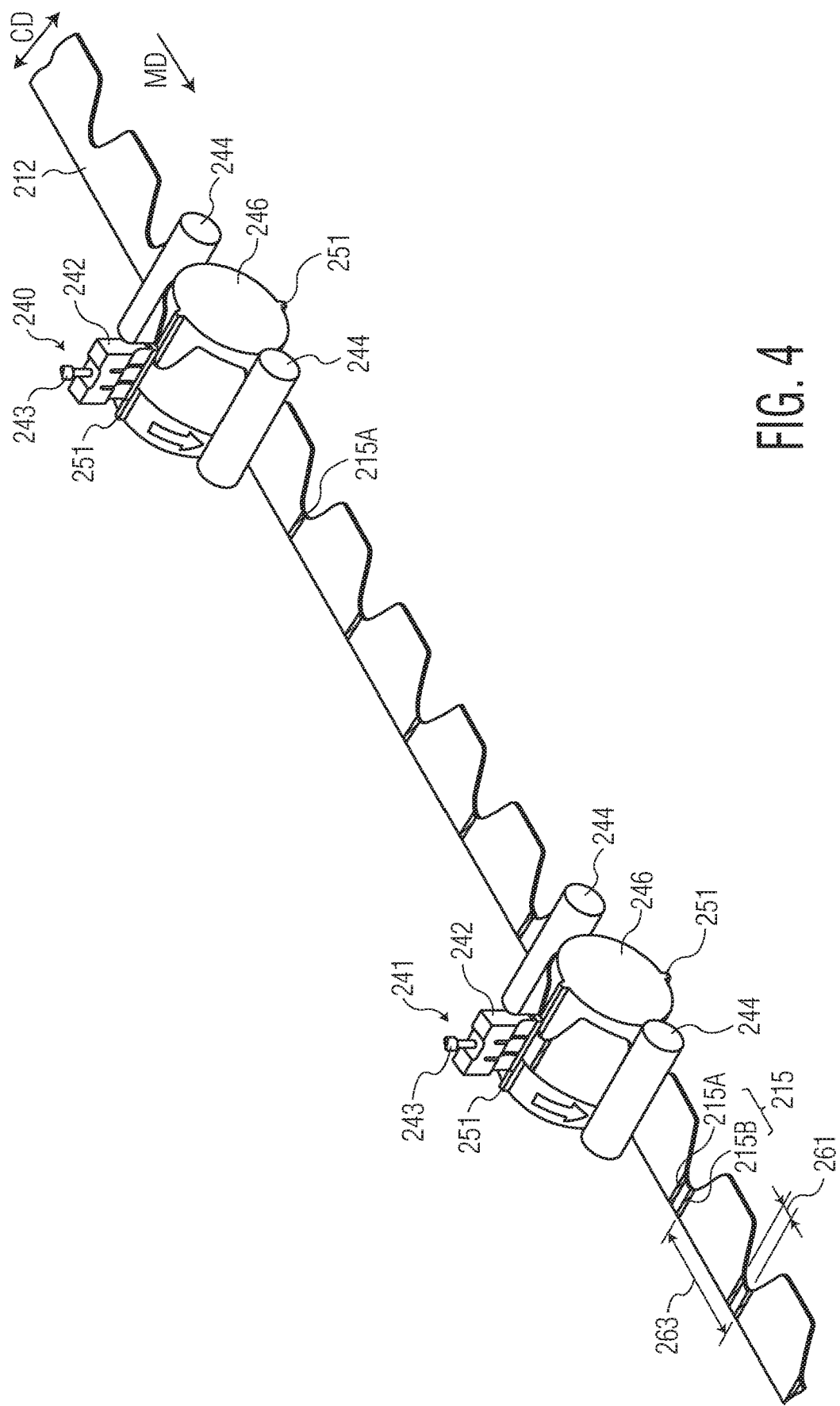
FIG. 4 is a perspective view of two bonding units for forming side seam bonds in absorbent articles, according to aspects of the present disclosure.
Figure 5:
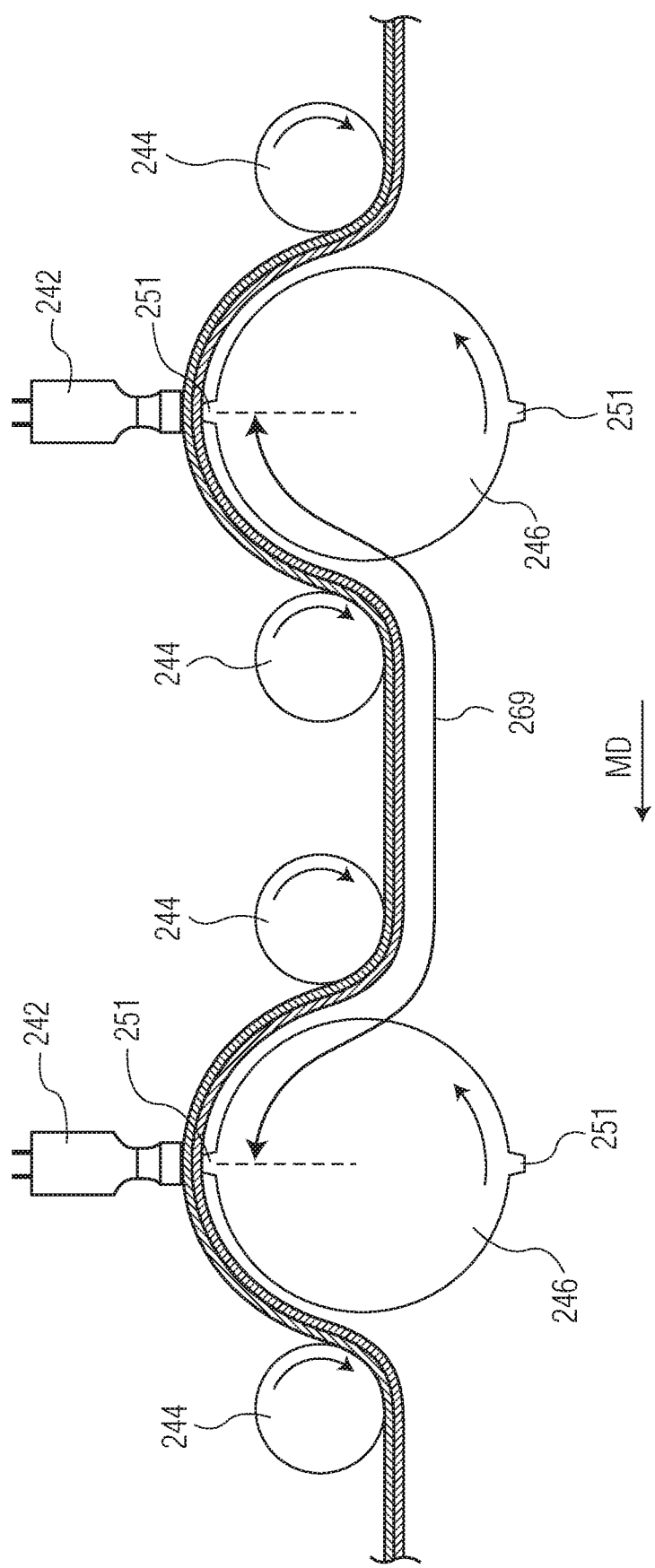
FIG. 5 is a plan front view of the two bonding units of FIG. 4.

FIG. 4 is a close-up perspective view of bonding units 240, 241 of the manufacturing method 200 of FIG. 3. Where the bonding units 240, 241 are ultrasonic bonding units, they may be comprised of ultrasonic horns 242 connected to an energy source or sources (not shown) through coupling 243, anvil rolls 246 having protrusions 251, guiding rolls 244. As described above, the first bonding unit 240 may form the first bonds 215A of bond pairs 215 at regular, repeating intervals on the continuously extending absorbent article chassis 12. In this manner, the first bonding unit 240 may form the first bonds 215A of a plurality of bond pairs 215 and allow the manufacturing process 200 to run in a continuous fashion. The second bonding unit 241 may also be configured to form the second bonds 215B of the bond pairs 215 at regular, repeating intervals on the chassis 12. The second bonds 215B are spaced apart a pitch distance 263, which may be the same as the spacing between the first bonds 215A. The pitch distance 263 may be set based on the particular size and shape of the absorbent articles 10' being manufactured. The second bonds 215B may be formed so as to have a spacing distance 261 with respect to the first bonds 215A. In general, it is beneficial to have small spacing distances 261 in order to reduce an amount of material bunched at the sides of each article 10' or which needs to be removed—both representing waste in the manufacture of the articles 10'.

As seen in FIG. 4, the first bonding unit 240 may be configured to always form the first bonds 215A of each of the bond pairs 215, which are the trailing bonds of the bond pairs 215 in the machine direction MD. In these embodiments, the second bonding unit 241 may be configured to always form the second bonds 215B of each of the bond pairs 215, which are the leading bonds of the bond pairs 215 in the machine direction MD. However, in other embodiments, this does not need to be the case. For example, in other embodiments according to the present disclosure, the first bonding unit 240 may be configured to alternate which of the bonds 215A, 215B the first bonding unit 240 forms for successive bond pairs 215. More specifically, the first bonding unit 240 may be configured to form the first bond 215A of a first bond pair 215 and the second bond 215B of a second, subsequent bond pair 215. The first bonding unit 240 may then repeat this pattern. In such embodiments, the second bonding unit 241 may then be configured to form the bonds 215A and 215B of successive bond pairs 215 in an opposite alternating pattern. For instance, the second bonding unit 241 may be configured to form the second bond 215B of the first bond pair 215 and the first bond 215A of the second bond pair 215, and then may continue forming bonds 215A, 215B in this repeating pattern.

In still further embodiments, the first bonding unit 240 and the second bonding unit 241 may be configured to form the bonds 215A and 215B in even more complex patterns. As one example, the first bonding unit 240 may be configured to form the first bond 215A of a first bond pair 215, the second bond 215B of a second bond pair 215 which is immediately subsequent to the first bond pair 215, the second bond 215B of a third bond pair 215 which is immediately subsequent to the second bond pair 215, and the first bond 215A of a fourth bond pair 215 which is immediately subsequent to the third bond pair 215. The first bonding unit 240 may be configured to repeat this pattern. The second bonding unit 241 may be configured to form the corresponding bonds 215B, 215A, 215A, and 215B in each of the first, second, third, and fourth bond pairs 215, and may be configured to repeat this pattern. In still other embodiments, the first bonding unit 240 and the second bonding unit 241 may be configured to form the bonds 215A and 215B in even more complex patterns. However, in whatever pattern the first bonding unit 240 and the second bonding unit 241 are configured to form the bonds 215A and 215B, the first bonding unit 240 may be configured to form only one of the bonds 215A, 215B of a bond pair 215 while the second bonding unit 241 may be configured to form the other of the bonds 215A, 215B of the bond pair 215.

Splitting the step of forming the side seam bond pairs 215 into two discrete bonding steps, eliminates many of the drawbacks of the prior art method 100 described with respect to FIG. 1. Currently available ultrasonic bonding equipment are not suitable to forming individual bonds in quick succession where each of the bonds have similar bond quality. It is believed that upon becoming energized and engaged to form a first bond, the ultrasonic horn of a bonding unit, such as ultrasonic horn unit 142, undergoes an amount of compression. Once the ultrasonic horn is de-energized, there is recovery period, defined by a length of time, in which the ultrasonic horn unit decompresses back to its steady state. If the ultrasonic horn is energized again to form a second bond before returning to its steady state, this second formed bond is generally of lower quality than the first formed bond. Accordingly, in order to maintain a minimum level of quality for the second bond in a bond pair, the speed of the absorbent article chassis 112 must be maintained at a speed slow enough for the second bond of a bond pair to be of a minimum sufficient quality.

According to the method 200, however, the first and second bonding units 240, 241 are not required to form bonds in quick succession, or in as quick of succession as the bonds are formed in the method 100. For instance, the spacing between the bonds 215A and/or 215B formed by the first and second bonding units 240, 241 is generally the pitch distance 263. Although, the exact distance may depend on the particular bond forming pattern used by the units 240, 241. In the method 100, the spacing between the bonds 215A, 215B formed by the bonding unit 140 is the spacing distance 261, which is much less than the pitch distance 263. This difference in distance translates to a longer time between when a bonding unit becomes energized to form a bond for the method 200, given the same web speed. Accordingly, the method 200 may allow for forming the bonds 215A, 215B having at least the minimum sufficient quality at higher web speeds than the method 100.

The method 200 may allow for forming bond pairs 215 with each of the bonds 215A, 215B having a minimum sufficient bond quality at web speeds in excess of 250 meters/minute (m/min), and even in excess of 300 m/min. In some specific examples, the method 200 may allow for formation of bonds 215A, 215B having a bond strength of at least 17 N, or at least 29 N, or at least 44 N, according the Bond Peel Strength Test Method described herein, while operating at web speeds in excess of 250 m/min and in excess of 300 m/min when bonding a variety of materials together. Some example materials include spunbond and spunbond-meltblown-spunbond (SMS) materials comprising polypropylene or polypropylene/polyethylene blends having basis weights between about 15 grams/square meter (gsm) and about 25 gsm, which may be bonded in any combination resulting in the above described bond strengths. Such example materials can be produced according to the method 200 using conventional ultrasonic bonding equipment, such as that commercially available from Hermann Ultrasonics, Inc., located at 1261 Hardt Circle Bartlett, Ill. 60103 with the pitch length 163 and the bond spacing distance 161 having conventional values in the adult care absorbent article garment field.

Further, the method 200 may allow for a more consistent bond strength between bonds 215A and 215B than the method 100. For example, the method 200 may allow for a difference in the values of the bond strengths of the bonds 215A, 215B to be no more than about 15%, or about 10%, or about 5%, of the value of the higher bond strength of the bonds 215A, 215B.

Bond Peel Strength Test Method:

This test method is designed to quantify the peak strength of the ultrasonic point bonds holding two materials together. The direction of removal (peel), in this application, is generally the direction that such bonds may be broken when used as side seams on absorbent articles.

Equipment

1. Tensile tester capable of obtaining a peak load and equipped with an appropriate load cell. A suitable tensile testing system is a Sintech Tensile Tester, commercially available from MTS Sintech, Research Triangle Park, N.C., under the trade designation Instron Model 4201 Tensile Tester with Sintech QAD (Quality Assurance Department) Software.
2. Software commercially obtained from MTS Sintech under the trade designation Sintech Testworks™.
3. Pneumatic-action grips commercially available from Instron Corporation, Canton, Mass., under the trade designation "Instron Model 2712-041."
4. 1 by 3 inch grip faces, serrated, commercially available from Instron Corporation, Canton, Mass.
5. Test facility having a temperature of 23±1° C., and a relative humidity of 50±2 percent.

Test Procedure
1. A sample to be tested is conditioned in the test facility for at least 4 hours prior to testing.
2. The load cell is calibrated and the software loaded.
3. The grips are installed on the tensile tester with the jaws closed.
4. The test condition for the tensile tester are set as follows:
    Crosshead speed: 508 millimeters/minute
    Full-scale load: Use an appropriate load cell for the material being tested so the test value falls between 5 and 95% of the full-scale load
    Break Sensitivity: 60 percent
    Gage length: 50 millimeters
5. The sample material is cut into 102 mm long strips, with one bond disposed between ends of the sample material.
6. The material is inserted into the upper jaw such that the material is centered between the ends of the jaw. The upper jaw is closed 7. The material is inserted into the lower jaw such that the material is centered between the ends of the jaw. The lower jaw is closed.
8. The crosshead is started in motion.
9. The peak load of failure is recorded in grams-force. Results are rejected if the place of failure is any location other than the ultrasonic point bonds.

Those skilled in the art will recognize that the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A method of forming absorbent articles;
advancing one or more continuous webs in a machine direction, a first region of the one or more continuous webs comprising a front waist panel material and a second region of the one or more continuous webs comprising a rear waist panel material;
coupling absorbent cores to the one or more continuous webs intermittently to form an interconnected series of open absorbent article chassis, each absorbent article chassis comprising a front waist panel, a rear waist panel, and an absorbent core extending between the front waist panel and the rear waist panel;
folding the interconnected series of open absorbent article chassis to form an interconnected series of closed absorbent article chassis;
forming a first side seam bond of a first side seam bond pair between the first region of the one or more continuous webs and the second region of the one or more continuous webs with a first ultrasonic horn;
forming a second side seam bond of the first side seam bond pair between the first region of the one or more continuous webs and the second region of the one or more continuous webs with a second ultrasonic horn, wherein the first side seam bond of the first side seam bond pair is associated with a first absorbent article chassis and wherein the second side seam bond of the first side seam bond pair is associated with a second absorbent article chassis; and
cutting the interconnected series of folded absorbent article chassis between the first side seam bond and the second side seam bond of the first side seam bond pair to separate the first absorbent article chassis from the second absorbent article chassis,
wherein the first ultrasonic horn forms only the first side seam bond of the side seam bond pair and the second ultrasonic horn forms only the second side seam bond of the side seam bond pair.

2. The method of claim 1, further comprising:
forming a first side seam bond of a second side seam bond pair between the first region of the one or more continuous webs and the second region of the one or more continuous webs with the first ultrasonic horn;
forming a second side seam bond of the second side seam bond pair between the first region of the one or more continuous webs and the second region of the one or more continuous webs with a second ultrasonic horn, wherein the first side seam bond of the second side seam bond pair is associated with the second absorbent article chassis and wherein the second side seam bond of the second side seam bond pair is associated with a third absorbent article chassis; and
cutting the interconnected series of folded absorbent article chassis between the first side seam bond of the second side seam bond pair and the second side seam bond of the second side seam bond pair to separate the second absorbent article chassis from the third absorbent article chassis,
wherein the first ultrasonic horn forms only the first bond or the second bond of the second side seam bond pair and the second ultrasonic horn forms only the other of first bond or the second bond of the second side seam bond pair.

3. The method of claim 1, further comprising:
forming a first side seam bond of a second side seam bond pair between the first region of the one or more continuous webs and the second region of the one or more continuous webs with the first ultrasonic horn;
forming a second side seam bond of the second side seam bond pair between the first region of the one or more continuous webs and the second region of the one or more continuous webs with a second ultrasonic horn, wherein the first side seam bond of the second side seam bond pair is associated with a third absorbent article chassis and wherein the second side seam bond of the second side seam bond pair is associated with the second absorbent article chassis; and
cutting the interconnected series of folded absorbent article chassis between the first side seam bond of the second side seam bond pair and the second side seam bond of the second side seam bond pair to separate the second absorbent article chassis from the third absorbent article chassis,
wherein the first ultrasonic horn forms only the first bond or the second bond of the second side seam bond pair and the second ultrasonic horn forms only the other of first bond or the second bond of the second side seam bond pair.

4. The method of claim 3, further comprising:
forming a first side seam bond of a third side seam bond pair between the first region of the one or more continuous webs and the second region of the one or more continuous webs with the first ultrasonic horn;
forming a second side seam bond of the third side seam bond pair between the first region of the one or more continuous webs and the second region of the one or more continuous webs with a second ultrasonic horn, wherein the first side seam bond of the third side seam bond pair is associated with the third absorbent article chassis and wherein the second side seam bond of the third side seam bond pair is associated with a fourth absorbent article chassis;
forming a first side seam bond of a fourth side seam bond pair between the first region of the one or more continuous webs and the second region of the one or more continuous webs with the first ultrasonic horn;
forming a second side seam bond of the fourth side seam bond pair between the first region of the one or more continuous webs and the second region of the one or more continuous webs with a second ultrasonic horn, wherein the first side seam bond of the fourth side seam bond pair is associated with a fifth absorbent article chassis and wherein the second side seam bond of the fourth side seam bond pair is associated with the fourth absorbent article chassis; and
cutting the interconnected series of folded absorbent article chassis between the first side seam bond of the third side seam bond pair and the second side seam bond of the third side seam bond pair and between the first side seam bond of the fourth side seam bond pair and the second side seam bond of the fourth side seam bond pair to separate the third absorbent article chassis from the fourth absorbent article chassis and the fourth absorbent article chassis from the fifth absorbent article chassis,
wherein the first ultrasonic horn forms only the first bond or the second bond of the third side seam bond pair and the second ultrasonic horn forms only the other of first bond or the second bond of the third side seam bond pair, and
wherein the first ultrasonic horn forms only the first bond or the second bond of the fourth side seam bond pair and the second ultrasonic horn forms only the other of first bond or the second bond of the fourth side seam bond pair.

5. The method of claim 3, further comprising:
forming a first side seam bond of a third side seam bond pair between the first region of the one or more continuous webs and the second region of the one or more continuous webs with the first ultrasonic horn;
forming a second side seam bond of the third side seam bond pair between the first region of the one or more continuous webs and the second region of the one or more continuous webs with a second ultrasonic horn, wherein the first side seam bond of the third side seam bond pair is associated with a fourth absorbent article chassis and wherein the second side seam bond of the third side seam bond pair is associated with the third absorbent article chassis;
forming a first side seam bond of a fourth side seam bond pair between the first region of the one or more continuous webs and the second region of the one or more continuous webs with the first ultrasonic horn;
forming a second side seam bond of the fourth side seam bond pair between the first region of the one or more continuous webs and the second region of the one or more continuous webs with a second ultrasonic horn, wherein the first side seam bond of the fourth side seam bond pair is associated with the fourth absorbent article chassis and wherein the second side seam bond of the fourth side seam bond pair is associated with a fifth absorbent article chassis; and
cutting the interconnected series of folded absorbent article chassis between the first side seam bond of the third side seam bond pair and the second side seam bond of the third side seam bond pair and between the first side seam bond of the fourth side seam bond pair and the second side seam bond of the fourth side seam bond pair to separate the third absorbent article chassis from the fourth absorbent article chassis and the fourth absorbent article chassis from the fifth absorbent article chassis,
wherein the first ultrasonic horn forms only the first bond or the second bond of the third side seam bond pair and the second ultrasonic horn forms only the other of first bond or the second bond of the third side seam bond pair, and
wherein the first ultrasonic horn forms only the first bond or the second bond of the fourth side seam bond pair and the second ultrasonic horn forms only the other of first bond or the second bond of the fourth side seam bond pair.

6. The method of claim 1, wherein the first side seam bond of the first side seam bond pair is formed by the first ultrasonic horn engaging a first anvil, and wherein the second side seam bond of the first side seam bond pair is formed by the second ultrasonic horn engaging with a second anvil.

7. The method of claim 6, wherein the second ultrasonic horn is spaced from the first ultrasonic horn a distance of at least 1.0 m in the manufacturing direction.

8. The method of claim 1, wherein the first side seam bond of the first side seam bond pair is formed by the first ultrasonic horn engaging a first anvil, and wherein the second side seam bond of the first side seam bond pair is formed by the second ultrasonic horn engaging with the first anvil.

9. The method of claim 8, wherein the first ultrasonic horn is spaced away from the second ultrasonic horn on the first anvil a circumferential distance greater than or equal to twenty-percent of the circumference of the first anvil.

10. The method of claim 1, wherein, when forming the first bond and the second bond of the first side seam bond pair, the first ultrasonic horn and the second ultrasonic horn remain stationary with respect to the machine direction.

11. The method of claim 1, wherein the first ultrasonic horn engages with a first protrusion of a first anvil to form the first bond of the first side seam bond pair, the first protrusion spaced from every other protrusion on the first anvil by a circumferential distance greater than or equal to twenty-percent of the circumference of the first anvil.

12. A method of forming absorbent articles;
advancing one or more continuous webs in a machine direction at a web speed, a first region of the one or more continuous webs comprising a front waist panel material and a second region of the one or more continuous webs comprising a rear waist panel material, wherein the web speed is greater than or equal to 250 m/min;
coupling absorbent cores to the one or more continuous webs intermittently to form an interconnected series of open absorbent article chassis, each absorbent article chassis comprising a front waist panel, a rear waist panel, and an absorbent core extending between the front waist panel and the rear waist panel;

folding the interconnected series of open absorbent article chassis to form an interconnected series of closed absorbent article chassis;

forming a first side seam bond of a first side seam bond pair between the first region of the one or more continuous webs and the second region of the one or more continuous webs with a first ultrasonic horn;

forming a second side seam bond of the first side seam bond pair between the first region of the one or more continuous webs and the second region of the one or more continuous webs with a second ultrasonic horn, wherein the first side seam bond of the first side seam bond pair is associated with a first absorbent article chassis and wherein the second side seam bond of the first side seam bond pair is associated with a second absorbent article chassis; and cutting the interconnected series of folded absorbent article chassis between the first side seam bond and the second side seam bond of the first side seam bond pair to separate the first absorbent article chassis from the second absorbent article chassis, wherein the first ultrasonic horn forms only the first side seam bond of the side seam bond pair and the second ultrasonic horn forms only the second side seam bond of the side seam bond pair, wherein the first side seam bond of the first side seam bond pair has a bond strength of greater than or equal to 17 N, according to the Bond Peel Strength Test Method, and wherein the second side seam bond of the first side seam bond pair has a bond strength of greater than or equal to 17 N, according to the Bond Peel Strength Test Method.

13. The method of claim 12, wherein the first side seam bond of the first side seam bond pair has a bond strength of greater than or equal to 29 N, according to the Bond Peel Strength Test Method, wherein the second side seam bond of the first side seam bond pair has a bond strength of greater than or equal to 29 N, according to the Bond Peel Strength Test Method.

14. The method of claim 12, wherein the web speed is greater than or equal to 300 m/min.

15. The method of claim 12, wherein the first side seam bond of the first side seam bond pair is formed by the first ultrasonic horn engaging with a first anvil roll, and wherein the second side seam bond of the first side seam bond pair is formed by the second ultrasonic horn engaging with a second anvil roll.

16. The method of claim 15, wherein the second ultrasonic horn is spaced from the first ultrasonic horn a distance of at least 1.0 m in the manufacturing direction.

17. The method of claim 12, wherein a difference between the bond strength of the first side seam bond of the first side seam bond pair and the second side seam bond of the first side seam bond pair is less than about 15% of the value of the greater of the bond strength of the first side seam bond of the first side seam bond pair and the second side seam bond of the first side seam bond pair.

18. The method of claim 12, wherein a difference between the bond strength of the first side seam bond of the first side seam bond pair and the second side seam bond of the first side seam bond pair is less than about 10% of the value of the greater of the bond strength of the first side seam bond of the first side seam bond pair and the second side seam bond of the first side seam bond pair.

19. The method of claim 12, wherein, when forming the first bond and the second bond of the first side seam bond pair, the first ultrasonic horn and the second ultrasonic horn remain stationary with respect to the machine direction.

20. The method of claim 12, wherein the first ultrasonic horn engages with a first protrusion of a first anvil to form the first bond of the first side seam bond pair, the first protrusion spaced from every other protrusion on the first anvil by a circumferential distance greater than or equal to twenty-percent of the circumference of the first anvil.

\* \* \* \* \*